US007062982B2

(12) United States Patent
Coyle et al.

(10) Patent No.: US 7,062,982 B2
(45) Date of Patent: Jun. 20, 2006

(54) METHOD AND APPARATUS FOR CONCENTRATED AIRBORNE PARTICLE COLLECTION

(75) Inventors: Peter J. Coyle, Newtown, PA (US); Timothy A. Pletcher, Eastampton, NJ (US); Timothy J. Davis, Columbus, NJ (US); Shakuntala Mangru, New Egypt, NJ (US)

(73) Assignee: Sarnoff Corporation, Princeton, NJ (US)

( * ) Notice: Subject to any disclaimer, the term of this patent is extended or adjusted under 35 U.S.C. 154(b) by 74 days.

(21) Appl. No.: 10/603,119

(22) Filed: Jun. 24, 2003

(65) Prior Publication Data

US 2004/0069047 A1 Apr. 15, 2004

Related U.S. Application Data

(60) Provisional application No. 60/390,974, filed on Jun. 24, 2002, provisional application No. 60/446,323, filed on Feb. 10, 2003.

(51) Int. Cl.
*G01N 1/24* (2006.01)
*G01N 1/40* (2006.01)

(52) U.S. Cl. ............... 73/863.23; 73/863.41; 73/863.71; 73/864; 73/864.91

(58) Field of Classification Search ............ 73/863.21, 73/863.22, 863.23, 863.24, 863.41, 863.51, 73/863.71, 864, 864.31, 864.51, 864.71, 73/864.91
See application file for complete search history.

(56) References Cited

U.S. PATENT DOCUMENTS

| | | | |
|---|---|---|---|
| 2,696,275 A | 12/1954 | Pring | 183/30 |
| 3,754,868 A | 8/1973 | Witz et al. | 23/254 R |
| 3,768,302 A | 10/1973 | Barringer | 73/28 |
| 4,000,995 A | 1/1977 | Morris | 55/282 |
| 4,169,714 A | 10/1979 | Calvert | 55/5 |
| 4,225,327 A | 9/1980 | Sgaslik et al. | 55/324 |
| 4,249,655 A | 2/1981 | Patureau et al. | 209/31 |
| 4,255,172 A | 3/1981 | Smith | 55/270 |
| 4,267,048 A | 5/1981 | Ohishi | 210/512.2 |

(Continued)

FOREIGN PATENT DOCUMENTS

CA 2164348 A * 6/1997

OTHER PUBLICATIONS

"Final Research Report—SBIR A002-0576 Phase I", Rocky Mountain Research Labs, Inc., Sep. 28, 2001.*

(Continued)

*Primary Examiner*—Charles Garber
*Assistant Examiner*—David A. Rogers
(74) *Attorney, Agent, or Firm*—Lowenstein Sandler PC

(57) ABSTRACT

An apparatus for collecting biological aerosols from an air sample is provided comprising an air intake assembly adapted to draw the air sample into the apparatus, a separation section coupled to the intake assembly and adapted to separate aerosol particles from the air sample, a capture section coupled to the separation section and adapted to transport the aerosol particles in a stream of liquid, and a hydrophobic membrane disposed between the separation section and the capture section and adapted to establish a controllable air/fluid boundary therebetween. Further embodiments of the apparatus comprise an air intake assembly adapted to draw the air sample into the apparatus, a separation section coupled to the intake assembly and adapted to separate aerosol particles from the air sample, a capture section coupled to the separation section and adapted to transport the aerosol particles in a stream of liquid, and a corona charging section disposed between the separation section and the capture section and adapted to focus the aerosol particles into the stream of liquid.

36 Claims, 9 Drawing Sheets

U.S. PATENT DOCUMENTS

| | | | |
|---|---|---|---|
| 4,350,507 A | 9/1982 | Greenough et al. | 55/270 |
| 4,606,232 A | 8/1986 | Prodl | 73/863.23 |
| 4,718,268 A | 1/1988 | Reid et al. | 73/23 |
| 4,734,109 A | 3/1988 | Cox | 55/92 |
| 4,941,899 A | 7/1990 | Liu | 55/270 |
| 5,380,437 A | 1/1995 | Bertoncini | 210/416.1 |
| 5,448,062 A | 9/1995 | Cooks et al. | 250/288 |
| 5,646,357 A | 7/1997 | Ogden et al. | 73/863.31 |
| 5,783,756 A * | 7/1998 | Xiong et al. | 73/863.23 |
| 5,919,356 A | 7/1999 | Hood | 210/85 |
| 5,942,699 A | 8/1999 | Ornath et al. | 73/863.21 |
| 6,082,179 A | 7/2000 | Jeon et al. | 73/28.04 |
| 6,101,886 A | 8/2000 | Brenizer et al. | 73/863.23 |
| 6,210,575 B1 | 4/2001 | Chase et al. | 210/304 |
| 6,217,636 B1 | 4/2001 | McFarland | 95/216 |
| 6,267,016 B1 * | 7/2001 | Call et al. | 73/863.22 |
| 6,468,330 B1 | 10/2002 | Irving et al. | 95/219 |
| 6,482,252 B1 | 11/2002 | Conrad et al. | 96/57 |
| 6,484,594 B1 * | 11/2002 | Saaski et al. | 73/863.21 |
| 6,499,337 B1 | 12/2002 | Hoffman | 73/61.72 |
| 6,520,034 B1 | 2/2003 | Masquelier et al. | 73/863.21 |
| 6,530,287 B1 | 3/2003 | Rodgers | 73/863.21 |
| 6,532,835 B1 | 3/2003 | Saaski et al. | 73/863.21 |
| 6,550,347 B1 | 4/2003 | Bradley | 73/863.21 |
| 6,589,323 B1 | 7/2003 | Korin | 96/223 |
| 6,729,196 B1 * | 5/2004 | Moler et al. | 73/863.22 |
| 2003/0222012 A1 * | 12/2003 | Lee et al. | 210/321.84 |
| 2004/0107782 A1 * | 6/2004 | Bradley et al. | 73/864.34 |

OTHER PUBLICATIONS

Copy of International Search Report dated Nov. 5, 2003 for corresponding PCT application, PCT/US03/20004.

* cited by examiner

US 7,062,982 B2

METHOD AND APPARATUS FOR CONCENTRATED AIRBORNE PARTICLE COLLECTION

CROSS REFERENCE TO RELATED APPLICATIONS

This application claims the priority of U.S. Provisional Patent Application No. 60/390,974, filed Jun. 24, 2002 (entitled "Ultra-High Concentrating Bio-Aerosol Collector"), and to U.S. Provisional Patent Application No. 60/446,323, filed Feb. 10, 2003 (entitled "Corona-Based Bio-Aerosol Collector"), both of which are herein incorporated by reference.

FIELD OF THE INVENTION

The present invention generally relates to the sampling of air, and more particularly relates to the collection of pathogen and aerosol particles from air samples.

BACKGROUND OF THE INVENTION

There is an increasing demand for air sampling systems for military, private or individual use that are capable of collecting aerosol and pathogen particles or spores. While current air sampling systems have been proven to function reliably, they are often quite large and thus not only consume a great deal of power, but also produce a lot of noise. These systems also tend to produce very large liquid samples, analyses of which can take several days or even weeks. Thus current air sampling systems are not practical for private or individual use, or for environments or circumstances in which analysis of an air sample must be performed quickly.

Therefore, there is a need in the art for a compact, high-efficiency bio-aerosol collector that can produce a relatively small volume of liquid sample for expedited analysis.

SUMMARY OF THE INVENTION

Embodiments of the invention generally provide an apparatus for collecting particles (for example, biological aerosol particles) from an air sample comprising an air intake assembly adapted to draw the air sample into the apparatus, a separation section coupled to the intake assembly and adapted to separate aerosol particles from the air sample, a capture section coupled to the separation section and adapted to transport the aerosol particles into a stream of liquid, and a hydrophobic membrane disposed between the separation section and the capture section and adapted to establish a controllable air/fluid boundary therebetween.

Further embodiments of the apparatus comprise an air intake assembly adapted to draw the air sample into the apparatus, a separation section coupled to the intake assembly and adapted to separate aerosol particles from the air sample, a capture section coupled to the separation section and adapted to transport the aerosol particles in a stream of liquid, and a corona charging section disposed between the separation section and the capture section and adapted to focus the aerosol particles into the stream of liquid.

BRIEF DESCRIPTION OF THE DRAWINGS

So that the manner in which the above recited embodiments of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

Embodiments of the invention generally provide a compact, lightweight, low power and low noise device capable of collecting respirable airborne particles and focusing them into a small liquid volume. In one embodiment, the device is capable of achieving a particle concentration in the range of approximately 1 to 10 microns, and can achieve sampling rates of up to approximately 1000 liters per minute (lpm).

Figure 1:
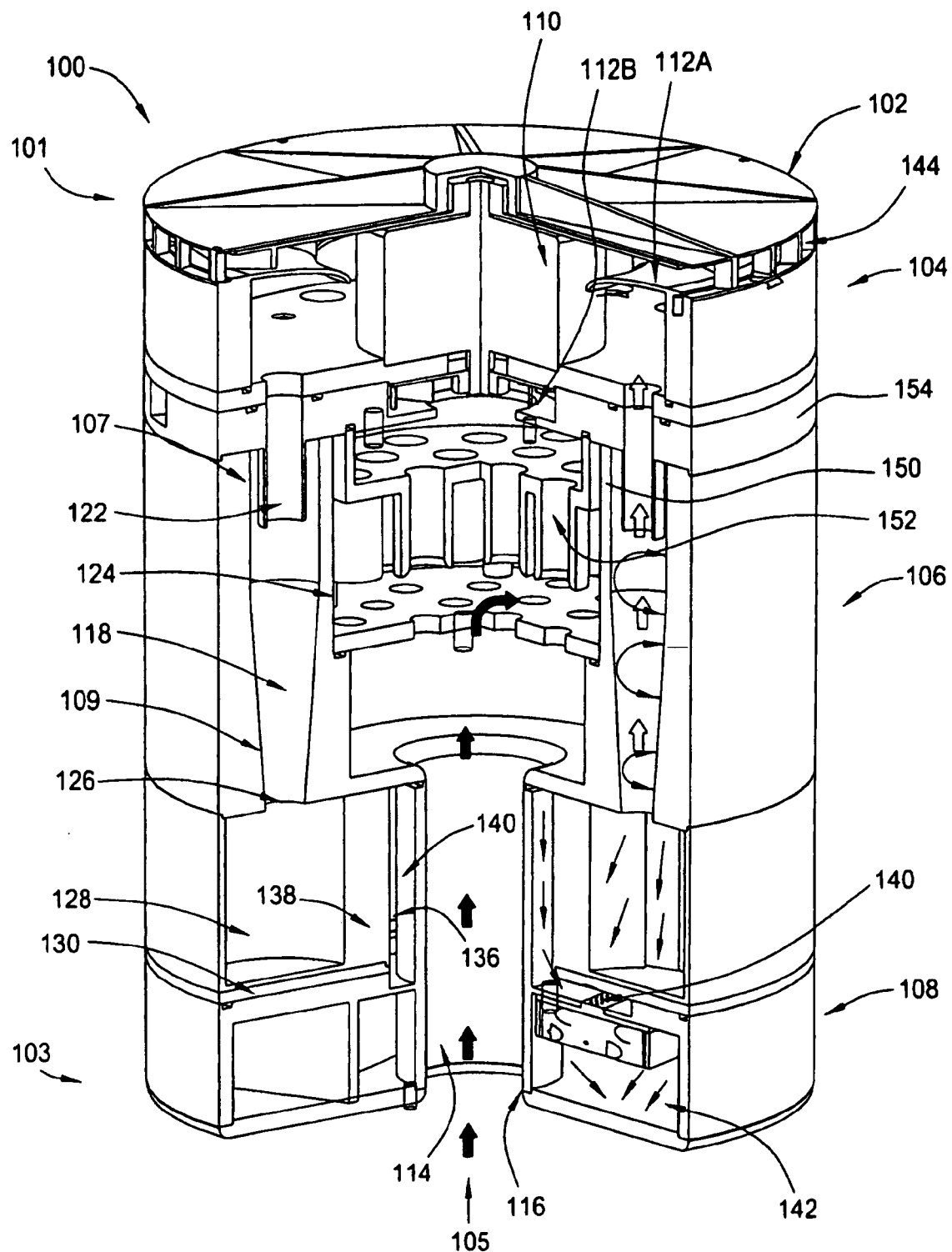
FIG. 1 is a cut away view of one embodiment of an airborne particle collection apparatus according to the present invention.

FIG. 1 is a cut away view of one embodiment of a particle collection apparatus 100 according to the present invention. In the embodiment illustrated, the apparatus 100 is constructed in a substantially cylindrical shape; however, those skilled in the art will appreciate that embodiments of the invention may be configured in any number of alternate forms and shapes without departing from the scope of the invention. The apparatus 100 comprises a housing 102, within which is contained an air intake assembly 104, a sample separation section 106, and a particle capture zone 108.

The air intake assembly 104 is adapted to draw air flow into the collection apparatus 100 and comprises a motor 110, first and second fans 112A, 112B, and an air duct 114. The first fan 112A is disposed proximate a first end 101 of the collection apparatus 100 and is coupled to the fan motor 110. The optional second fan 112B is positioned inward of the first fan 112A along a longitudinal axis of the apparatus 100, and in one embodiment, the second fan 112B is smaller than the first fan 112A. The air duct 114 begins at an aperture 116 in the second end 103 of the apparatus 100 and extends at least partially therethrough to provide an inlet path for the air that is drawn in by the fans 112A, 112B when in operation. In one embodiment, the duct 114 is disposed through the center 105 of the housing 102. Optionally, the air intake assembly 104 may further comprise an impactor 150 positioned between the duct 114 and the fans 112A, 112B and adapted to act as a pre-filter. That is, the impactor 150 includes a plurality of tubes or channels 152 for filtering large particles out of the primary flow as it is drawn into the apparatus 100.

Figure 2:
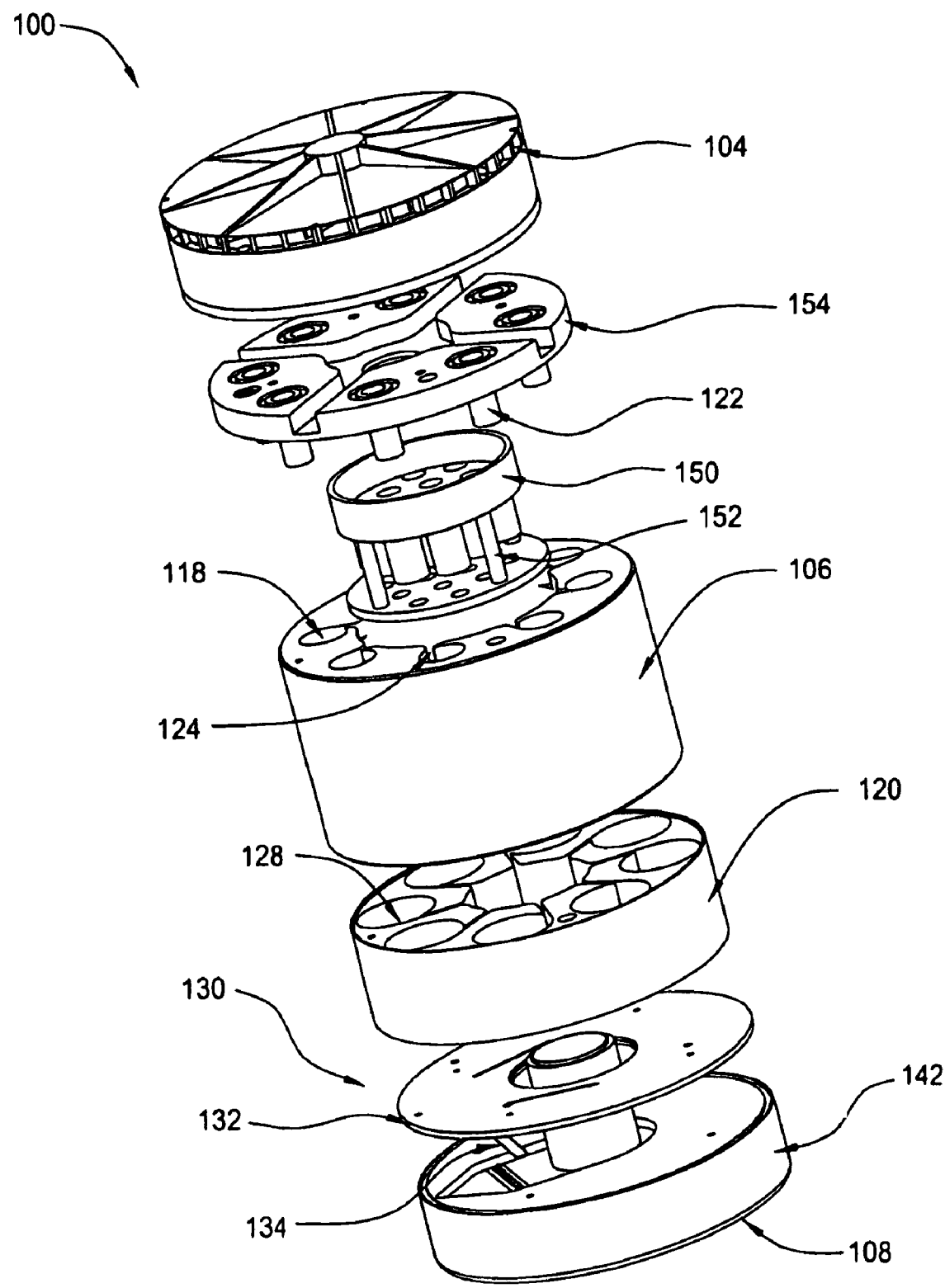
FIG. 2 is an exploded view of the airborne particle collection apparatus illustrated in FIG. 1.
Figure 4:
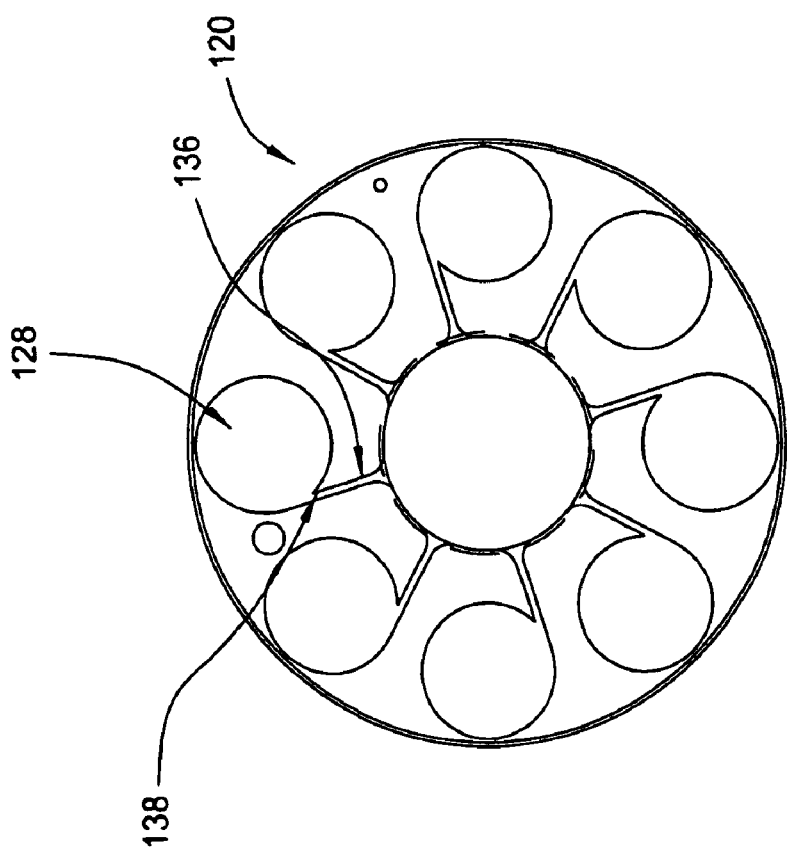
FIG. 4 is a top view of the vortex breaker section illustrated in FIG. 1.
Figure 3:
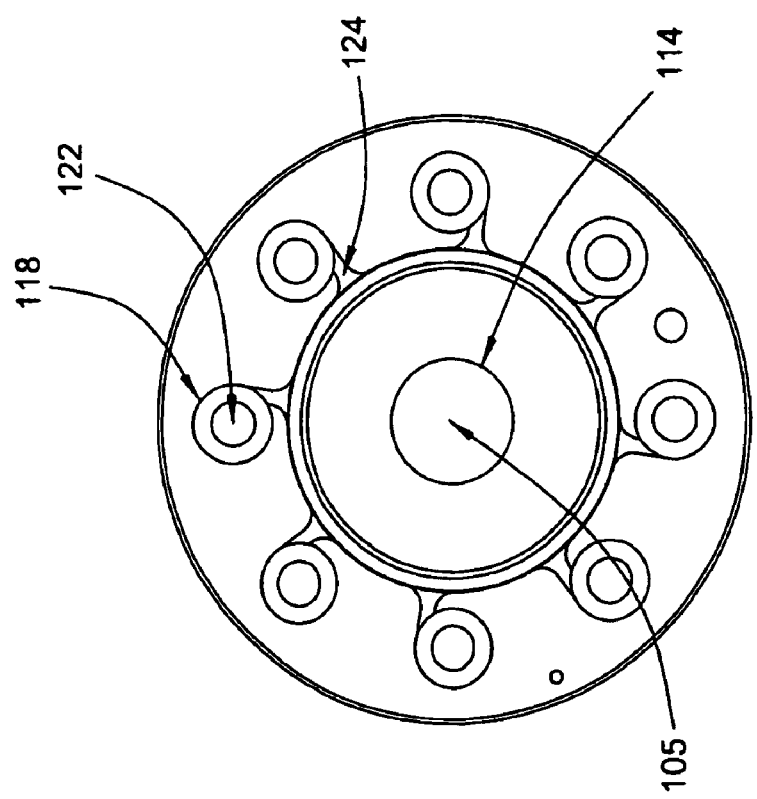
FIG. 3 is a top view of the cyclone array illustrated in FIG. 1.
Figure 5:
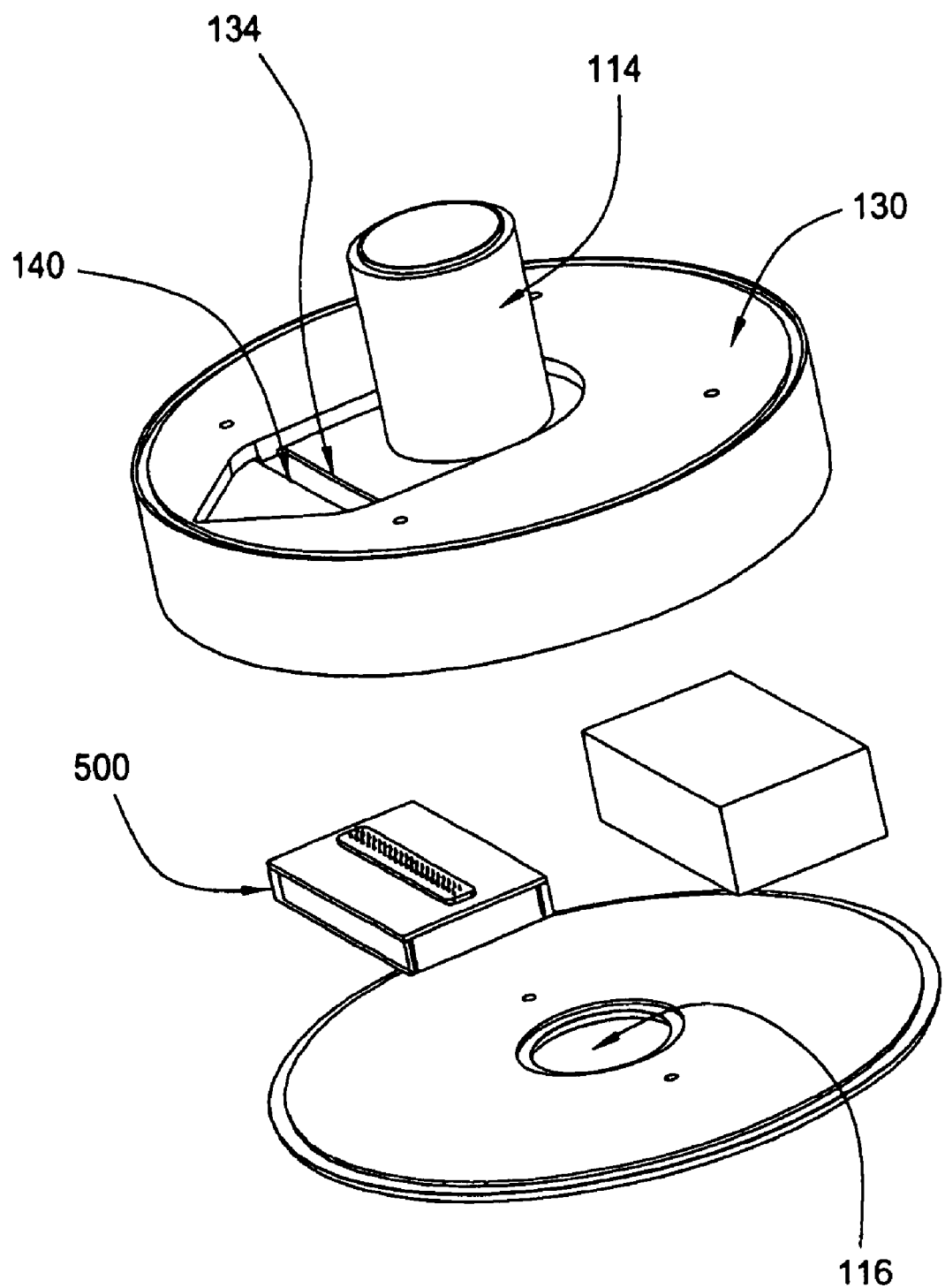
FIG. 5 is an exploded view of the capture section illustrated in FIG. 1.
Figure 7:
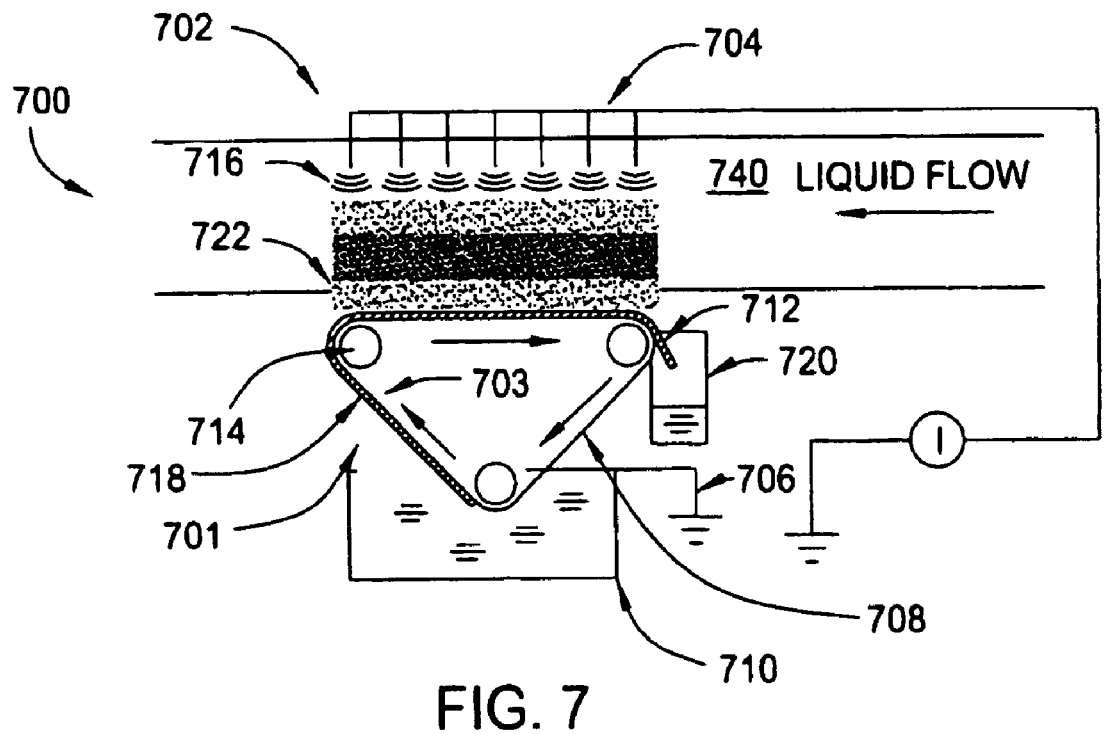
FIG. 7 is a second embodiment of a capture section and corona charging section.
Figure 6:
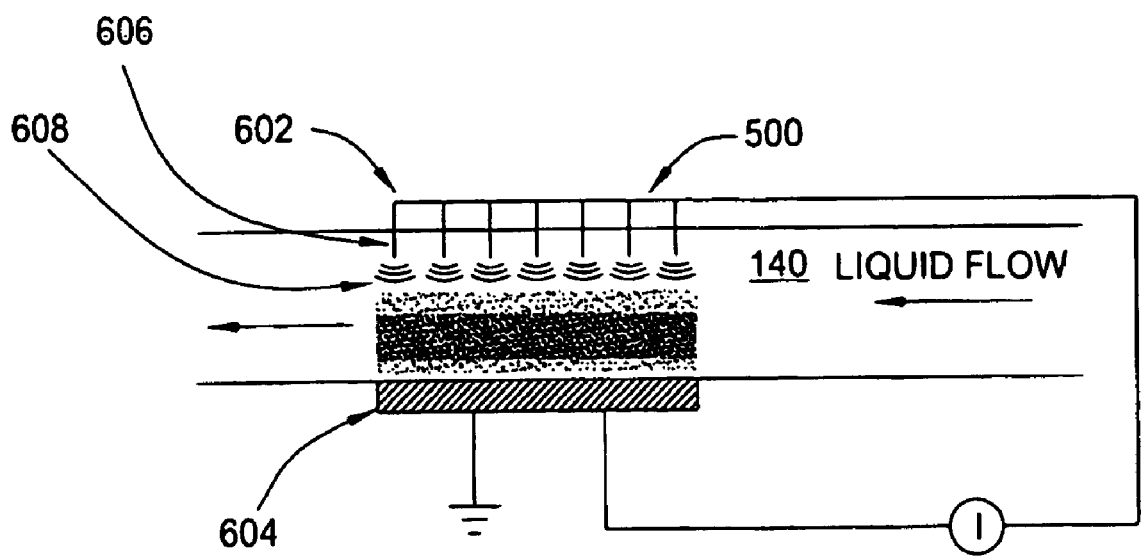
FIG. 6 is a schematic illustration of corona charging section adapted for use with the capture section illustrated in FIGS. 1 and 5.

The sample separation section 106 comprises a substantially circular array of cyclones 118 positioned radially outward of the center 105 of the apparatus 100 (i.e., in the embodiment illustrated in FIG. 1, radially outward of the air duct 114) and a vortex breaker 120 (shown in FIGS. 2 and 4). FIG. 3 is a top view of the cyclone array illustrated in FIG. 1. Although FIG. 3 depicts an array of eight cyclones 118, those skilled in the art will appreciate that a greater or lesser number of cyclones 118 may also be used to advantage. Referring simultaneously to FIGS. 1 and 3, each cyclone 118 in the array is connected to the air duct 114 by a tangential inlet 124. The inlets 124 are adapted to carry incoming air from the duct 114 to the sample separation section 106. Each cyclone 118 is adapted to separate airborne particles from the primary air flow. A vortex finder 154 positioned proximate to the first ends 107 of the cyclones 118 comprises a plurality of short channels that project into the cyclones 118 to establish first exits ports 122 for the primary flow. That is, a first exit port 122 at the first end 107 of each cyclone 118 is adapted to collimate and guide the primary flow out of the cyclones 118, so that the primary flow may be discharged from the separation section 106. A second exit port 126 located proximate a second end 109 of each cyclone 118 carries the separated particle flow to the vortex breaker 120.

Referring to FIGS. 1, 2 and 4, the vortex breaker 120 is located proximate the second ends 109 of the cyclones 118 and in one embodiment comprises a series of chambers 128. One chamber 128 is positioned adjacent the second end 109 of each cyclone 118 and has an interior volume adapted to concentrate the particle flow carried from the cyclones 118 into a relatively denser, low velocity flow. Alternatively, one chamber (not shown) may be substantially annular in shape and be adapted to receive aerosol flow from all cyclones 118. A tangential slot 136 in a wall 138 of the vortex chamber 128 allows the aerosol flow to be drawn out of the chamber 128 and toward the capture section 108.

The vortex breaker 120 is separated from the capture section 108 by a controllable air/fluid boundary 130. The air/fluid boundary 130 is positioned adjacent the exterior of the vortex chambers 128, and in one embodiment the mechanism comprises a liquid plate 132 having a high porosity hydrophobic membrane 134 disposed thereon. The hydrophobic membrane 134 is adapted to establish a liquid seal or boundary between the vortex chamber 128, which is adapted to contain air or particle flow (i.e., a gaseous medium), and the capture section 108, which is adapted to contain a liquid as described further herein. In one embodiment, the membrane 134 comprises a nylon mesh that is thermally imbedded over at least a portion of the capture section 108. The nylon mesh is optionally treated with polytetrafluoroethylene (PTFE) or an equivalent substance to increase its hydrophobic properties.

Referring to FIGS. 1 and 5, the capture section 108 comprises at least one microfluidic, or nanofluidic, channel 140 within which a small volume of liquid is contained for transporting the aerosol or other particles that have been focused therein. In one embodiment, a nylon mesh such as that described above is thermally embedded over the at least one channel 140. The capture section 108 may additionally comprise a liquid collection chamber 142, where the liquid flow (including the particles focused therein) is collected, or may alternatively be coupled to a means for transporting the flow to a separate analysis or collection device (not shown).

The air/fluid boundary 130 described above optionally includes an electrostatic focusing mechanism such as a corona charging section 500 for electrostatically manipulating the particles to enhance the focusing of the particles into the liquid in the at least one channel 140 of the capture section 108. One embodiment of a corona charging section 500 is illustrated in a schematic view in FIG. 6. The corona charging section 500 comprises a corona array 602 and a ground electrode 604. The corona array 602 comprises a plurality of corona tips 606 positioned proximate to the at least one channel 140 of the capture zone 108. The electrode 604 is positioned a distance away from the array, and in one embodiment is positioned across the channel 140 from the array 602. An electrostatic field 608 is thereby generated between the array 602 and the electrode 604. The electrostatic field 608 charges the particles in the liquid flow and drives them toward the middle of the channel 140. The corona charging section 500 is thereby adapted to enhance the manipulation of the particles into the liquid by urging the particles into the center of the liquid flow for quicker and more efficient transport. The electrostatic field generated by the corona charging section 500 also ensures a substantially uniformly charged particle stream.

FIG. 7 is a schematic view of a second embodiment of a collection section 700 including a corona charging section 702. In this embodiment, the collection section 700 includes a corona array 704 and electrode 706, a translating particle-collecting material such as a tape 708, a reservoir 710 and a particle removal device 712. In one embodiment, the collection tape 708 has a first surface 701 and a second surface 703, and is adapted to translate around several bearings 714 (e.g., three or more) in a closed loop. In one embodiment, the closed loop resembles a triangle. The corona array 704 and electrode 706 generate an electrostatic field 716 that drives particles through an aperture 722 in the channel 740 and onto the adjacent first surface 701 of the collection tape 708. The reservoir 710 is positioned adjacent the lower bearing or bearings 714 and is adapted to wick a thin layer 718 of fluid onto a first surface 701 of the tape 708 as it translates past or through the reservoir 710. The liquid layer 718 enhances collection of aerosol particles on the tape surface 701. The particle removal device 712 is positioned to remove particles from tape 708 after particles have been deposited, but before the tape 708 translates past the reservoir 710. The collection device 712 may be a squeegee, a blade, a vacuum or any other device that is capable of removing the liquid layer 718 from the tape 708 so that the liquid and particles therein are transferred to a collection chamber 720. Optionally, the first surface 701 of the tape 708 is treated to become hydrophilic, and the second surface 703 is treated to become hydrophobic. The area of the collection tape 708 may be very small to enable higher concentration of particles.

FIG. 9 is a schematic illustration of a third embodiment of a capture section 900 according to the present invention. The capture section 900 comprises a channel 902, a hydrophobic membrane 904, an electrostatic focusing electrode 906 and an electrophoretic electrode 908. The hydrophobic membrane 904 is substantially similar to that described previously herein, but is additionally made to be conductive and is embedded over a portion of the channel 902 adjacent the vortex breaker section (not shown). The electrophoretic electrode 908 is positioned across the channel 902 from the hydrophobic membrane 904. The electrostatic focusing electrode 906 is positioned outside of the channel 902, proximate the side on which the electrophoretic electrode 908 is positioned. A differential voltage V is applied across the channel 902 to create an electrophoretic pumping cell within the channel 902, between the hydrophobic membrane 904 and the electrophoretic electrode 908. An electrostatic effect created by the electrostatic focusing electrode 906 enhances the particle manipulation through the hydrophobic membrane 904 and into the liquid flow. The electrophoretic effect created by the pumping cell charges the particles in the liquid flow and drives them toward the center of the liquid flow for quicker and more efficient transport. In the event that there is interference between the electrostatic and electrophoretic effects, the two competing effects can be operated in a cyclic manner at an established optimum frequency that allows efficient electrostatic transport in the particle flow and also allows electrophoretic transport of the particles in the liquid flow.

FIG. 8 illustrates another embodiment of the present invention, in which a collection apparatus 800 also includes an electrostatic precipitator section 802. In one embodiment, the electrostatic precipitator section 802 comprises a plurality of precipitator plates 804 and at least one corona electrode 806, both located proximate the entries 801 (i.e., the first ends) of the cyclones 810. The electrostatic precipitator section 802 is adapted to attract small charged particles (i.e., charged within the cyclones 810 by the at least one corona electrode 806) that escape from the cyclones 810 along with the exiting primary flow rather than pass to the capture section 808.

Referring back to FIG. 1, in operation, the intake assembly 104 is activated to draw air into the apparatus 100 through the air duct 114. The air passes through the duct 114 to the tangential inlets 124, which carry the air flow to the the cyclones 118.

The cyclones 118 separate particles from the primary air flow. As the flow field is rapidly revolved within the cyclone 118, centrifugal force drives the aerosol particles to the walls of the cyclone 118, where the particles may be tribo-charged by rubbing against the wall surface. As the flow continues to spiral through the cyclone 118 to the second end 109, additional particles are separated from the flow. The flow of aerosol particles exits the cyclones 118 through the second ends 109 and enters the chamber 128 of the vortex breaker 120, where it is concentrated into a denser, low velocity flow.

The primary flow reverses direction and flows back through the centers of the cyclones 118, where it passes out of the first ends 107 of the cyclones 118 and is carried past the fans 112A, 112B and through exhaust ports 144 in the first end 101 of the housing 102, to exit the collection apparatus 100. If a precipitator section such as that illustrated in FIG. 8 is incorporated, small charged particles that are not separated out of the primary flow by the cyclones 118 will be attracted to precipitator plates as the primary flow passes through the precipitator plates on the way to the exhaust ports 144. The use of an array of small cyclones 118 (rather than, for example, a single large cyclone) to separate the aerosol and primary flows provides improved separation efficiency at a low pressure drop, thereby enabling the construction of a quieter and more compact apparatus 100 that consumes less power. For example, in one embodiment, the entire apparatus 100 is only six inches in diameter.

The densified aerosol flow is drawn through the tangential slots 136 in the walls 138 of the vortex breaker chambers 128. As the particles flow outward from the chambers 128, the particles are electrostatically focused into an array of capillaries formed by the hydrophobic mesh membrane 134. The particles are drawn through the capillaries in the mesh 134 and into the liquid of the capture section 108, where a continuous liquid flow through the microfluidic channels 140 transports the captured particles into the collection chamber 142. Alternatively, the capture section 108 may be coupled to a port or line (not shown) that is adapted to transport the fluid out of the collection apparatus 100 and into, for example, a separate collection container or an analysis device.

As the flow of particles arrives at the air/liquid interface (i.e., the hydrophobic membrane 134), the particles reside in a boundary layer where the liquid flow velocity approaches zero. Particle transport in the liquid is enhanced by positioning the corona electrode (604 in FIG. 6) adjacent the collection chamber 142, but isolated from the collection liquid. In this manner, the electrostatic field 608 continues to act upon the particles after they have entered the collection liquid in the microfluidic channels 140 of the capture section 108, which urges the particles into the higher velocity flow in the central portions of the channels 140 so that the particles can be rapidly carried away. This positioning of the electrode 604 also alleviates the need to bias the liquid in the channels 140 to a high voltage to attract the aerosol particles. Other means for enhancing particle transport in the liquid include, but are not limited to, electro-kinetic pumping, pulsed pumping, ultrasonic techniques and incremental pumping.

Over the course of operation, the hydrophobic mesh membrane 134 may become clogged with large particles, dust or debris. In such an instance, the water in the channels 140 may be pressurized to a level exceeding the retention pressure of the mesh membrane 134. Consequently, the boundary established by the membrane 134 will be broken and water will flow out through the mesh 134, carrying dust and debris away with the flow. The water pressure is subsequently reduced, allowing the mesh membrane 134 to re-establish the liquid seal. Thus the hydrophobic membrane 134 may be easily cleaned without having to disassemble the collection apparatus 100.

Although a collection apparatus according to the present invention has been heretofore described as a device having a substantially cylindrical configuration, those skilled in the art will appreciate that a collection apparatus may be constructed in alternate shapes and configurations without departing from the scope of the invention. For example, FIGS. 10A–10B illustrate an embodiment of a collection apparatus 1000 having a substantially box-shaped housing 1002.

The collection apparatus 1000 is constructed as a box having an air inlet side 1004 for the intake of air samples and an air outlet side 1006 opposite the inlet side 1004 for the expulsion of separated primary flow air. The inlet and outlet sides 1004, 1006 have a plurality of apertures 1010 for the intake or expulsion of air. In addition, at least one capture liquid outlet 1008 may be coupled to the housing 1002 to transport liquid and particles captured therein to a collection or analysis device (not shown).

As illustrated in FIG. 10B, the collection apparatus 1000 comprises an air intake section 1018, a separation section 1012, a vortex breaker section 1014 and a capture section 1016. The air intake section comprises a plurality of channels 1020 coupled to the apertures 1010 formed in the air inlet side 1004 of the housing 1002. Each channel 1020 has a tangential inlet 1022 that is coupled to the separation section 1012 for transporting air samples to the separation section 1012.

As in the previous embodiments, the separation section 1012 comprises at least one cyclone 1024 coupled to the inlets 1022 for receiving air samples and separating airborne particles in the samples from the primary flow. The at least one cyclone expels clean primary flow through a first exit port 1040, and expels separated particles through a second exit port 1026.

The second exit port 1026 transports the separated particles to a chamber 1028 of the vortex breaker section 1014, where the particle flow is concentrated for passage to the capture section 1016.

Figure 10A:
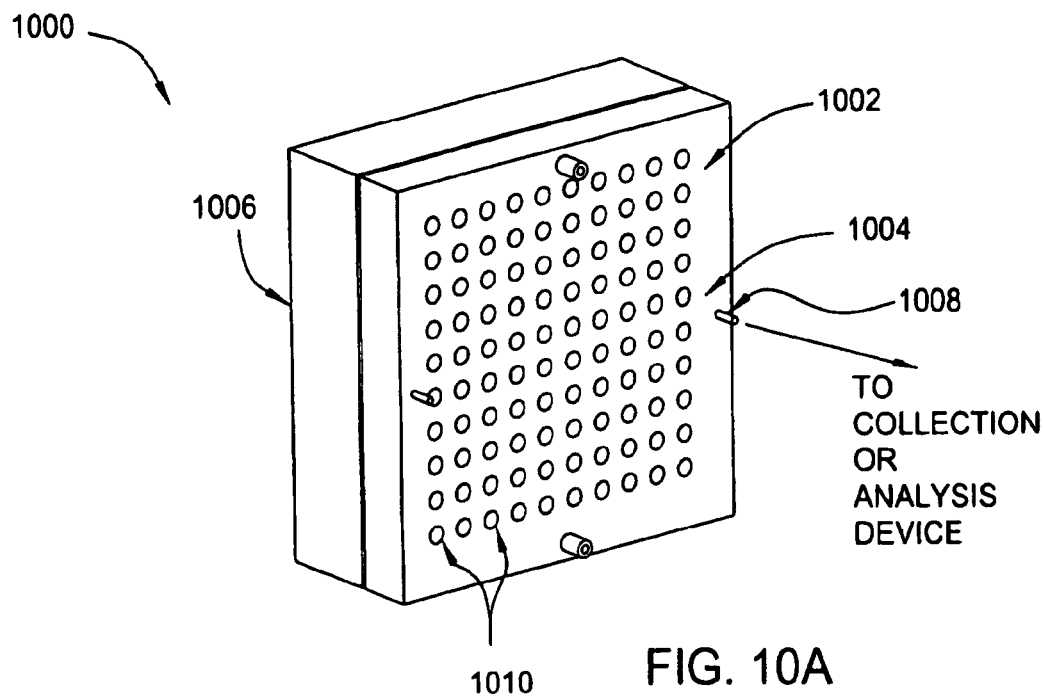
FIG. 10A is a plan view of a third embodiment of a collection apparatus according to the present invention.
Figure 10B:
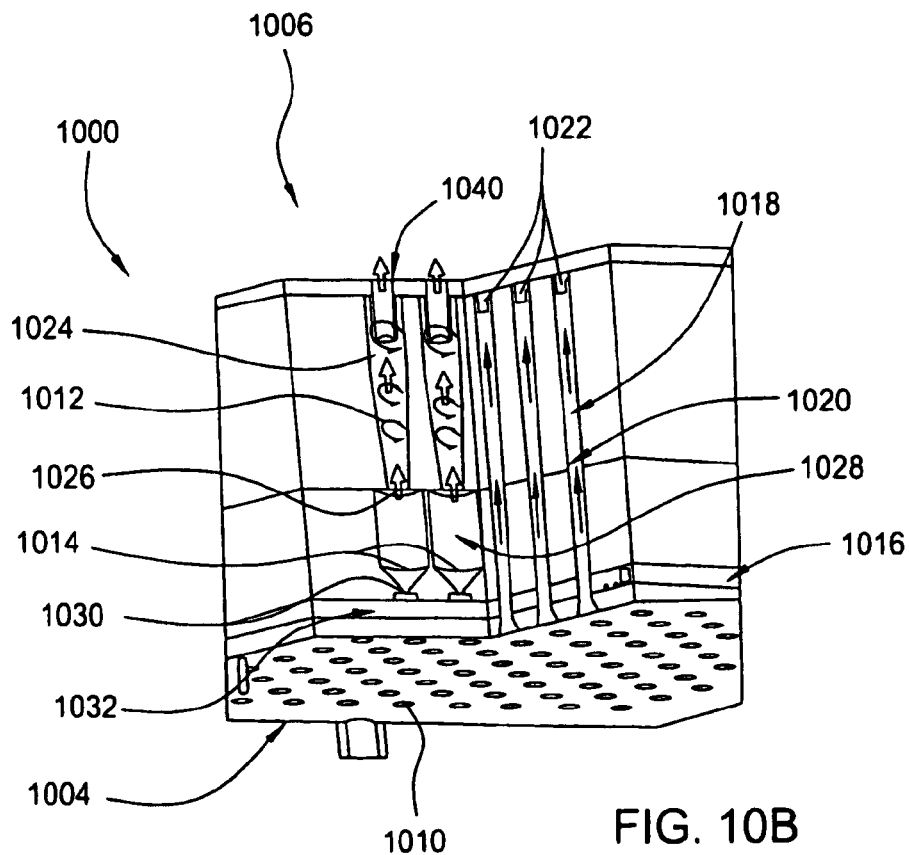
FIG. 10B is a cut away view of the collection apparatus illustrated in FIG. 10A.

The capture section 1016 is coupled to the vortex breaker section 1014. Concentrated particle flow is passed through an exit port 1030 in the vortex chamber 1028 to a capture section channel 1032. The channel 1032 contains a liquid for transporting the particles to a collection or analysis device (i.e., via the capture liquid outlet 1008 illustrated in FIG. 10A). Electrostatic focusing mechanisms such as the hydrophobic mesh and/or corona biasing assembly discussed herein may be used to enhance particle manipulation in the channel 1032.

Figure 8:
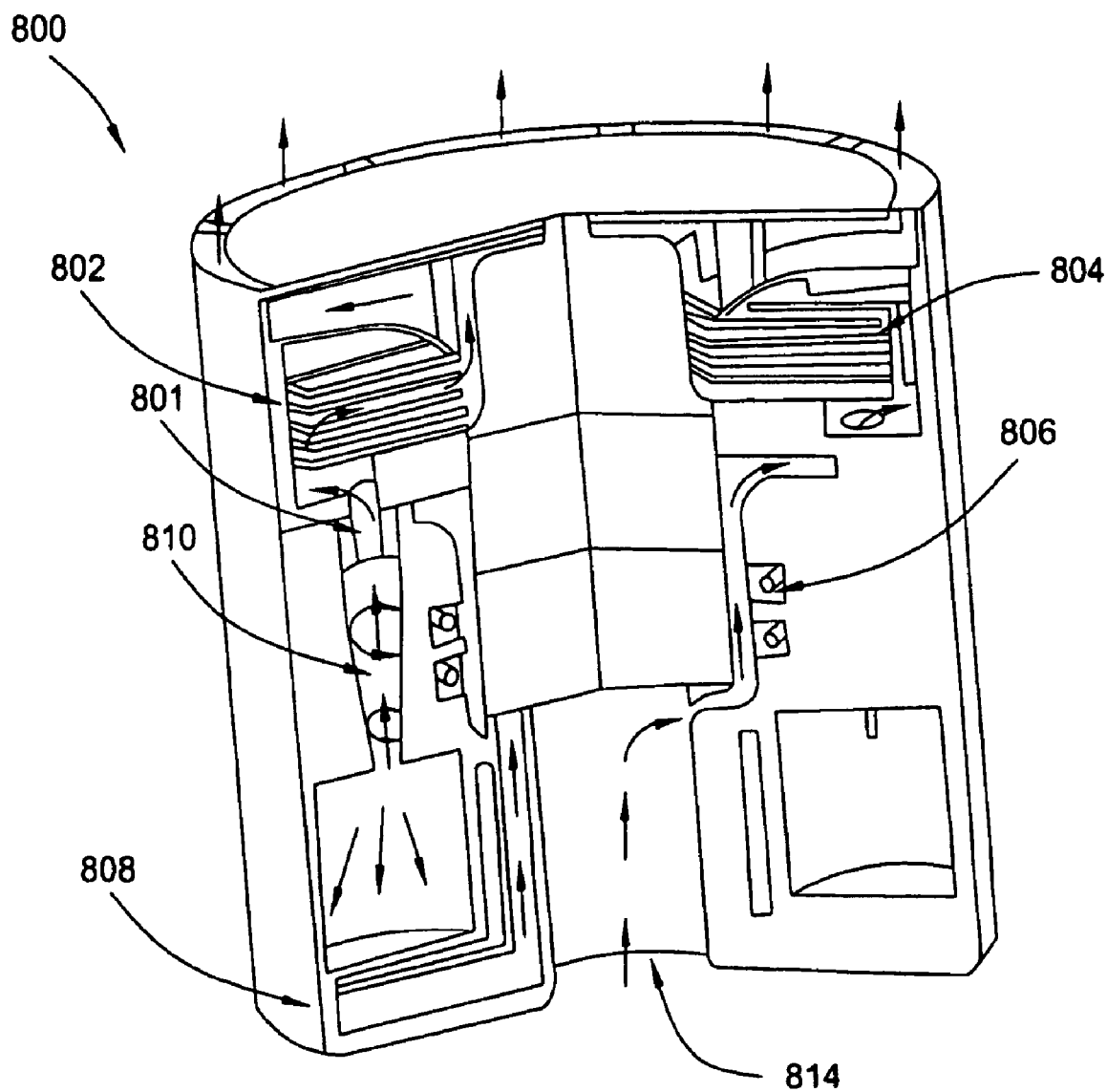
FIG. 8 is a second embodiment of a collection apparatus according to the present invention.
Figure 9:
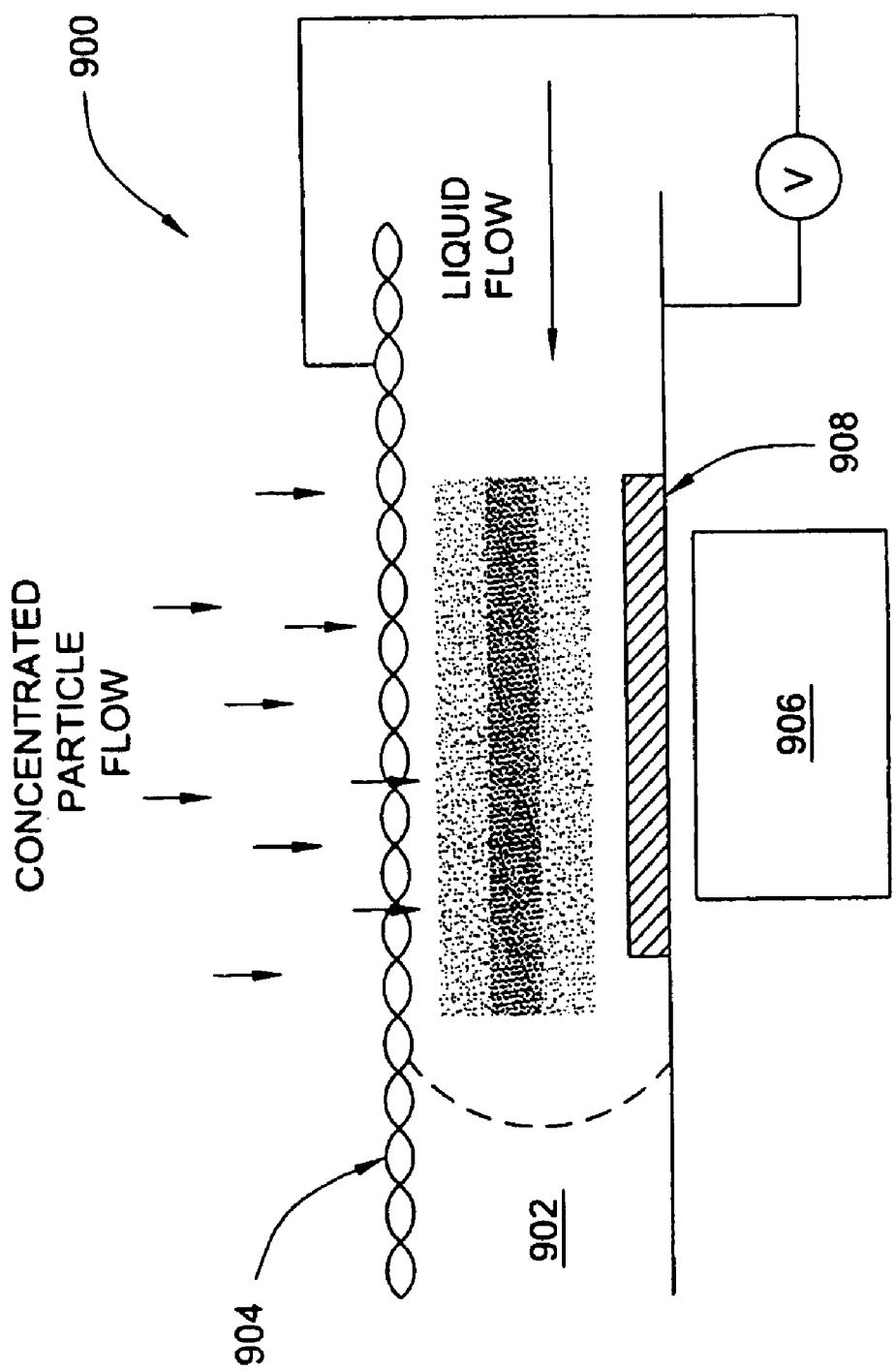
FIG. 9 is a schematic illustration of a third embodiment of a capture section according to the present invention.
Figure 11:
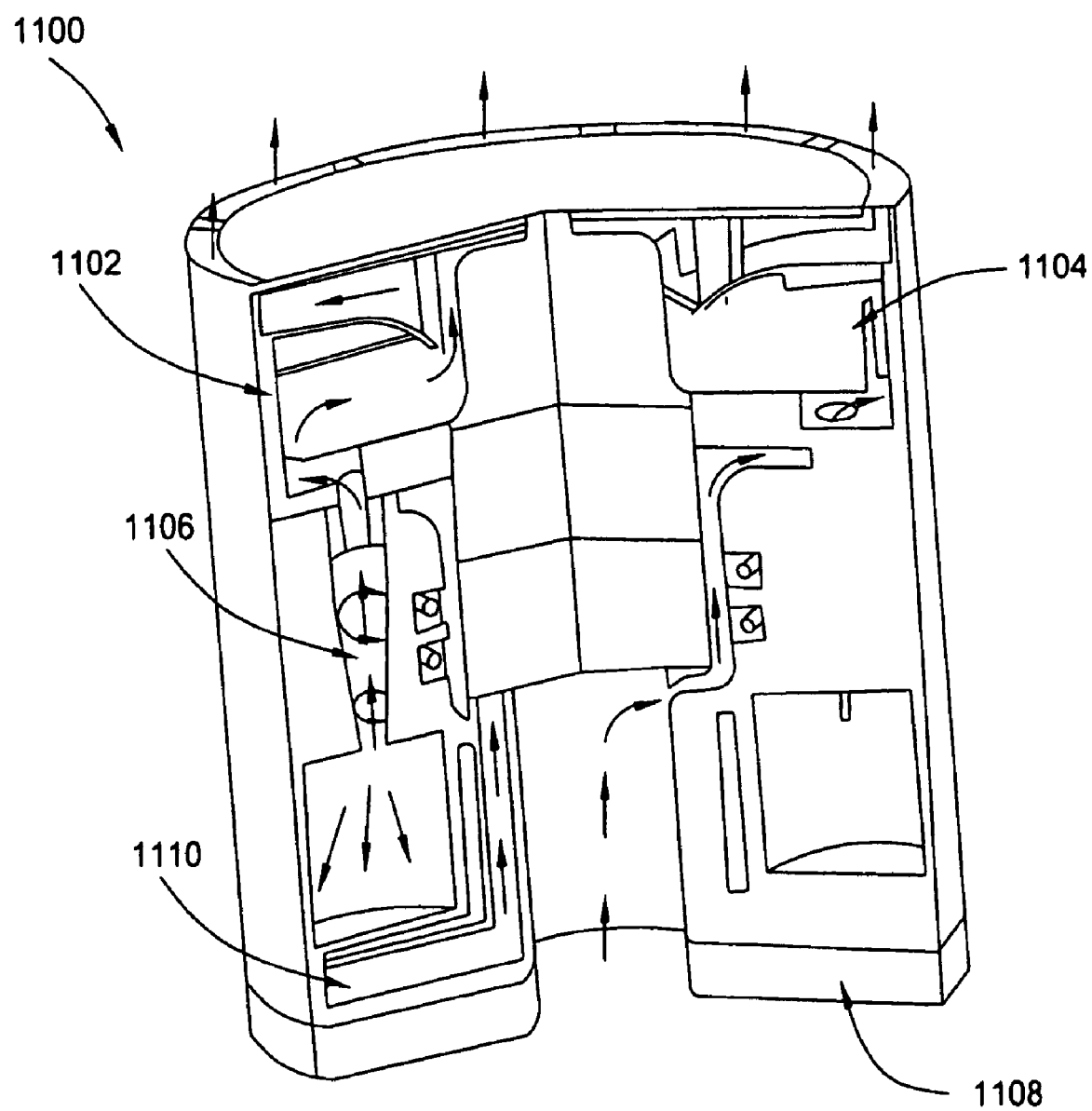
FIG. 11 is a cut away view of a fourth embodiment of a collection apparatus according to the present invention.

A fourth embodiment of a collection apparatus according to the present invention is illustrated in FIG. 11. The collection apparatus 1100 is substantially similar to the apparatus 800 illustrated in FIG. 8, but instead of an electrostatic precipitator section, the apparatus 1100 includes a condensation section 1102. In one embodiment, the condensation section 1102 comprises an evacuable volume 1104 that is adapted to cool and condense small airborne particles that escape from the cyclones 1106 along with the exiting primary flow. The condensation section 1102 may be adapted for coupling to an analysis or extraction device (not shown), for example by a port or connection that transports the condensed particles out of the apparatus 1100. Optionally, the apparatus 1100, or any of the alternate embodiments described herein, may include a detector section 1108 located adjacent to the capture section 1110 for retaining a device (not shown) to analyze the particles collected and condensed within the capture section 1110. The analysis device may be formed integral with the apparatus 1100, or the detector section 1108 may be manufactured for interface with a number of separate compatible analysis devices.

Thus, the present invention represents a significant advancement in the field of bio-aerosol collection. An apparatus is provided that achieves high air-sampling rates coupled with high concentration ratios, while minimizing power consumption, size, noise and consumables. Efficiency is further promoted by an air-to-liquid interface membrane that is easily cleaned to enable substantially clog-free operation of the apparatus.

While the foregoing is directed to embodiments of the invention, other and further embodiments of the invention may be devised without departing from the basic scope thereof, and the scope thereof is determined by the claims that follow.

What is claimed is:

1. An apparatus for collecting airborne particles comprising:
    an air intake assembly for drawing an air sample into the apparatus;
    a separation section coupled to the air intake assembly for separating particles from the air sample;
    a capture section coupled to the separation section for transporting the separated particles in a liquid; and
    a hydrophobic membrane disposed between the separation section and the capture section for establishing a controllable boundary therebetween.

2. The apparatus of claim 1, wherein the apparatus is adapted to produce a particle concentration factor for particles in a range of approximately one to ten microns.

3. The apparatus of claim 1, wherein the hydrophobic membrane comprises an array of capillaries.

4. The apparatus of claim 1, wherein the apparatus further comprises an electrostatic precipitator section comprising:
    a corona electrode positioned substantially between the intake assembly and the separation section; and
    a plurality of charged precipitator plates disposed proximate to a first end of the separation section.

5. The apparatus of claim 1, wherein the air intake assembly comprises:
    a first fan positioned proximate a first end of the apparatus;
    a motor coupled to the first fan; and
    an air duct disposed through the apparatus, wherein the air duct extends from an aperture in a second end of the apparatus and along at least part of a longitudinal axis of the apparatus.

6. The apparatus of claim 5, further comprising a second fan positioned inward from the first fan along the longitudinal axis of the apparatus.

7. The apparatus of claim 5, wherein the air intake assembly further comprises an impactor for removing large particles from the air sample.

8. The apparatus of claim 1, wherein the separation section comprises:
    at least one cyclone, wherein the at least one cyclone has a first end for receiving the air sample; and
    a vortex breaker section positioned proximate to a second end of the at least one cyclone for concentrating the particles.

9. The apparatus of claim 8, wherein the at least one cyclone further comprises:
    a primary flow exit port proximate to the first end of the at least one cyclone; and
    a particle exit port proximate to the second end of the at least one cyclone.

10. The apparatus of claim 8, wherein the separation section comprises eight cyclones disposed radially outward of a center of the apparatus.

11. The apparatus of claim 1, wherein the capture section comprises at least one channel disposed adjacent to the separation section, where said liquid is disposed in the at least one channel.

12. The apparatus of claim 11, wherein the at least one channel is microfluidic or nanofluidic.

13. The apparatus of claim 11, wherein the capture section further comprises a liquid collection chamber coupled to the at least one channel.

14. The apparatus of claim 11, wherein the at least one channel is adapted to transport said liquid to at least one of a fluid collection or fluid-particle analysis device.

15. The apparatus of claim 11, further comprising an electrophoretic pumping cell for manipulating the particles into the liquid in the at least one channel.

16. The apparatus of claim 11, wherein the liquid is electrostatically charged by a corona charging section comprising:
    a plurality of corona tips disposed proximate to the at least one channel; and a grounding electrode positioned a distance away from the plurality of corona tips.

17. The apparatus of claim 16, wherein the grounding electrode is electrically isolated from the capture section.

18. The apparatus of claim 16, wherein the capture section further comprises a particle collection apparatus comprising:
a loop of particle-collecting material positioned adjacent an aperture in the at least one channel;
a plurality of bearings for translating the loop of particle-collecting material;
a liquid reservoir for depositing a liquid layer onto a first surface of the particle-collecting material, wherein the liquid layer is for collecting the separated particles thereon when the particle-collecting material translates past the aperture in the at least one channel;
a fluid collection chamber for collecting the liquid layer and separated particles disposed thereon; and
a particle removal device positioned adjacent to the loop of particle-collecting material for removing the liquid layer and separated aerosol particles from the particle-collecting material and transferring the liquid and separated particles into the fluid collection chamber.

19. The apparatus of claim 18, wherein said first surface of the particle-collecting material is treated to be hydrophilic.

20. The apparatus of claim 19, wherein a second surface of the particle-collecting material is treated to be hydrophobic.

21. The apparatus of claim 1, wherein the hydrophobic membrane is comprised of a fluid-repellant mesh.

22. The apparatus of claim 21, wherein the mesh is formed of nylon.

23. The apparatus of claim 22, wherein the mesh is treated with polytetrafluoroethylene.

24. A system for analyzing airborne particles comprising:
a particle collection apparatus adapted to collect airborne particles comprising:
an air intake assembly for drawing an air sample into the apparatus;
a separation section coupled to the intake assembly for separating particles from the air sample;
a capture section coupled to the separation section for transporting the separated particles in a liquid; and
a hydrophobic membrane disposed between the separation section and the capture section for establishing a controllable air/fluid boundary therebetween; and
a particle analysis device coupled to the collection apparatus for receiving a liquid sample from the capture section.

25. The system of claim 24, wherein the air intake assembly comprises:
at least a first fan positioned proximate to a first end of the apparatus;
a motor coupled to the at least first fan;
an air duct disposed through the apparatus, wherein the air duct extends from an aperture in a second end of the apparatus and along at least part of a longitudinal axis of the apparatus; and
an impactor positioned proximate to an end of the air duct distal from the aperture in the second end of the apparatus, wherein the impactor is for removing large particles from the air sample.

26. The system of claim 24, wherein the separation section comprises:
at least one cyclone, wherein the at least one cyclone has a first end for receiving the air sample; and
a vortex breaker section positioned proximate to a second end of the at least one cyclone for concentrating the particles.

27. The system of claim 24, wherein the hydrophobic membrane comprises
an array of capillaries.

28. The system of claim 24, wherein the hydrophobic membrane is comprised of a fluid-repellant mesh.

29. The system of claim 24, wherein the capture section comprises at least one channel disposed adjacent to the separation section, where said liquid is disposed in the at least one channel.

30. The system of claim 29, wherein the at least one channel is coupled to the particle collection chamber or the particle analysis device.

31. A method for collecting airborne particles, comprising the steps of:
collecting an air sample;
separating the air sample into a particle flow and a primary air flow;
concentrating the particle flow; and
passing the separated particle flow through a hydrophobic membrane and into a liquid.

32. The method of claim 31, wherein the step of separating the air sample further comprises the step of expelling the primary air flow into an outside environment.

33. The method of claim 31, wherein the step of passing the particle flow into the liquid flow further comprises the step of electrostatically charging the liquid flow.

34. The method of claim 31, wherein the step of passing the particle flow into the liquid flow further comprises the step of electrophoretically manipulating the particles into the liquid.

35. The method of claim 31, further comprising the step of removing debris from the hydrophobic membrane.

36. The method of claim 35, wherein the step of removing debris from the hydrophobic membrane comprises the steps of:
pressurizing the liquid flow to a level that is greater than a retention pressure of the hydrophobic membrane;
allowing the liquid flow to remove and transport debris lodged in the membrane; and
reducing the water pressure to a level at which the membrane is enabled to re-establish an air-liquid seal.

* * * * *